United States Patent
Tanno et al.

(10) Patent No.: US 6,559,134 B2
(45) Date of Patent: May 6, 2003

(54) SOLID PREPARATION CONTAINING LOW-SUBSTITUTED HYDROXYPROPYL CELLULOSE AND PRODUCTION PROCESS THEREOF

(75) Inventors: Fumie Tanno, Niigata-ken (JP); Sakae Obara, Niigata-ken (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 09/811,046

(22) Filed: Mar. 16, 2001

(65) Prior Publication Data

US 2001/0031734 A1 Oct. 18, 2001

(30) Foreign Application Priority Data

Mar. 17, 2000 (JP) .......................... 2000-075092

(51) Int. Cl.$^7$ .................. A61K 31/715; C08B 11/08
(52) U.S. Cl. .................. 514/57; 536/30; 536/95
(58) Field of Search .................. 514/57; 536/91, 536/84, 85, 56, 57, 30, 95

(56) References Cited

U.S. PATENT DOCUMENTS

| | | | |
|---|---|---|---|
| 4,305,502 A | 12/1981 | Gregory et al. | |
| 5,501,861 A | 3/1996 | Makino et al. | |
| 5,720,974 A | 2/1998 | Makino et al. | |

FOREIGN PATENT DOCUMENTS

| | | |
|---|---|---|
| EP | 0 487 774 A | 6/1992 |
| EP | 0 957 112 A2 * | 11/1999 |
| JP | 8 291051 A | 11/1996 |
| JP | 9 048726 A | 2/1997 |
| JP | 9 071523 A | 3/1997 |
| WO | WO 98/11878 | 3/1998 |
| WO | WO98/53798 | 12/1998 |
| WO | WO 00/06126 A | 2/2000 |
| WO | WO 00/06126 * | 2/2000 |

OTHER PUBLICATIONS

United StateS Pharmacopeia, 25$^{th}$ Ed., pp. 1981–1982 (2001).*
"Low–Substituted Hydroxypropylcellulose as a Sustained–Drug Release Matrix Base oR Disintegrant Depending on its Particle Size and Loading in Formulation" Kawashima et al. Pharm. Res. 10(3) 1993 pp. 351–355.*
Database WPI, Section Ch, Week 199718, Derwent Publications Ltd. London, GB; Class A96, AN 1997–196011 XP002168961 & JP 08 291051 A (Sato Seiyaku KK), Nov. 5, 1996.

* cited by examiner

Primary Examiner—Richard L. Raymond
Assistant Examiner—Zachary C. Tucker
(74) Attorney, Agent, or Firm—Alston & Bird LLP

(57) ABSTRACT

Provided are a solid preparation which rapidly disintegrates in the oral cavity when taken together with the saliva in the oral cavity or a small amount of water, can be prepared easily and has strength enough to retain its formability upon production or during distribution; and a production process of the solid preparation. Specifically, provided are a solid preparation comprising a low-substituted hydroxypropyl cellulose having a loose bulk density of 0.40 g/ml or greater and a tapped bulk density of 0.60 g/ml or greater, and a sugar and/or sugar alcohol; and a production process of the solid preparation. Also provided are a solid preparation comprising a low-substituted hydroxypropyl cellulose having a volume-average particle size as measured by the dry laser diffraction method of 25 μm or less which is obtained by pulverizing a low-substituted hydroxypropyl cellulose having a loose bulk density of 0.40 g/ml or greater, a tapped bulk density of 0.60 g/ml or greater, and a volume average particle size of 30 μm or greater—and a sugar and/or sugar alcohol; and a production process of the solid preparation.

4 Claims, No Drawings

SOLID PREPARATION CONTAINING LOW-SUBSTITUTED HYDROXYPROPYL CELLULOSE AND PRODUCTION PROCESS THEREOF

BACKGROUND OF THE INVENTION

1. Field of the Invention

The present invention relates to a solid preparation which disintegrates rapidly in the oral cavity with saliva or a small amount of water.

2. Description of the Related Art

In recent years, there is a demand for the development of an easily-taken and easily-administrable solid preparation for aged or pediatric patients who have difficulty in swallowing. Specific examples of such a solid preparation include orally disintegrating preparations, jellied preparations and paste preparations. Among them, orally disintegrating preparations can be taken conveniently and comparatively easily without water or with a small amount of water so that it can be a dosage form suited for the aged or infant.

A variety of orally disintegrating preparations have so far been proposed. For example, an orally disintegrating tablet prepared by filling PTP (Press Through Package) with an aqueous solution of an active ingredient and a polymer such as gelatin and then lyophilizing it, and a production process thereof are proposed in Japanese Patent Publication (JP-B) No. 62-50445/1987. This process, however, requires a special preparation step and in addition, the tablet thus prepared involves a problem in handling because of its insufficient strength.

In Japanese Patent Provisional Publication (JP-A) No. 5-271054/1993, proposed are an orally disintegrating tablet obtained by tableting kneaded material containing an active ingredient, a sugar and a proper amount of water under a low pressure and then drying it, and a production process thereof. This process is not suited for mass production, because the kneaded material tends to adhere to a mortar or pestle upon tableting and difficulty is encountered in water control in the production step.

In Japanese Patent Provisional Publication (JP-A) No. 8-291051/1996 or 9-48726/1997, proposed are an orally disintegrating tablet obtained by tableting a mixture of a sugar and/or sugar alcohol, a water-soluble binder, an active ingredient and the like under a low pressure, wetting the resulting tablet under moistening conditions for heightening the strength of it and then drying, and a production process thereof. This process, however, is accompanied with the problems that it requires many steps, a change in the appearance of the tablet during the moistening step impairs its commodity value and moreover, this process is not suited for an active ingredient not stable under humid conditions or an active ingredient exhibiting deliquescence.

Some processes which do not require such a special production technique but use ordinarily employed equipment have been proposed. In Japanese Patent Provisional Publication (JP-A) No. 9-71523/1997, proposed is an orally disintegrating tablet obtained by tableting, under a low pressure, a mixture comprising an active ingredient, a low-substituted hydroxypropyl cellulose as a disintegrator, crystalline cellulose as an excipient and a lubricant. This tablet, however, is inferior in practice, for example, in disintegration, solubility, texture (a feeling on the tongue) and taste owing to a large amount of a cellulose or polyvinyl pyrrolidone additive contained in it.

In Japanese Patent Provisional Publication (JP-A) No. 11-43429/1999, an orally disintegrating tablet comprising an active ingredient, a sugar and a low-substituted hydroxypropyl cellulose having a limited degree of substitution is proposed, but it has not satisfactorily improved texture or taste.

SUMMARY OF THE INVENTION

An object of the present invention is to provide a solid preparation which rapidly disintegrates in the oral cavity when taken together with the saliva in the oral cavity or a small amount of water, can be prepared easily and has strength enough to retain its form or moldability upon production or during distribution; and a production process of the solid preparation.

Finding that a solid preparation comprising a low-substituted hydroxypropyl cellulose having a loose bulk density of 0.40 g/ml or greater and a tapped bulk density of 0.60 g/ml or greater, and a sugar and/or sugar alcoho; has enough strength, is free from unpleasant taste in the oral cavity and permits rapid disintegration of the active ingredient, the present inventors have completed the present invention.

In one aspect of the present invention, there is thus provided a solid preparation comprising a low-substituted hydroxypropyl cellulose having a loose bulk density of 0.40 g/ml or greater and a tapped bulk density of 0.60 g/ml or greater and a sugar and/or sugar alcohol; and a production process of the solid preparation.

In another aspect of the present invention, there is also provided a solid preparation comprising a low-substituted hydroxypropyl cellulose having a volume average particle size, as measured by the dry laser diffraction method, of 25 μm or greater which is obtained by pulverizing a low-substituted hydroxypropyl cellulose having a loose bulk density of 0.40 g/ml or greater, a tapped bulk density of 0.60 g/ml or greater, and a volume average particle size of 30 μm or greater as measured by the dry laser diffraction method; and a sugar and/or sugar alcohol; and a production process of the solid preparation.

The solid preparation according to the present invention can easily be taken by the aged or infant having weak swallowing power, because it is excellent in formability or moldability and disintegration.

DETAILED DESCRIPTION OF THE PREFERRED EMBODIMENTS

The term "loose bulk density" as used herein means the bulk density under a roughly filled state and it is determined by uniformly feeding a sample, downwards from the height of 23 cm, to a cylindrical container (material: stainless, capacity: 100 ml) of 5.03 cm in diameter and 5.03 cm in height through a 24-mesh sieve specified in Japanese Industrial Standard (JIS), leveling its upper surface and weighing one level container of the sample.

On the other hand, the term "tapped bulk density" as used herein means the bulk density under a densely filled state with the aid of tapping. The term "tapping" as used herein means an operation of dropping a container filled with a sample from a predetermined height in repetition to give a light impact on the bottom of the container, thereby filling the container with the sample densely. In practice, after the loose bulk density is determined by weighing one level container of the sample, a cap (a fixture of the below-described "Powder Tester", product of Hosokawa Micron Corporation) is put on the container, the sample powders were added up to the upper edge of the cap and then tapping from the height of 1.8 cm is conducted 180 times. After completion of the tapping, the cap is removed, the upper surface of the container is leved, and one level container of the powders is weighed as "tapped bulk density". The above-described operations can be conducted using "Powder Tester PT-D" (trade name; product of Hosokawa Micron Corporation).

The low-substituted hydroxypropyl cellulose to be used in the present invention has a loose bulk density of 0.40 g/ml or greater and a tapped bulk density of 0.60 g/ml or greater, preferably that available by pulverizing a low-substituted hydroxypropyl cellulose having the above-described bulk densities and in addition, having a volume average particle size, as measured by the dry laser diffraction method, of 30 $\mu$m or greater. Pulverization may be conducted in a conventional manner, for example, by using a pulverizer such as ball mill, hammer mill, knife mill or jet mill.

The term "dry laser diffraction method" as used herein means a method, like that using an HELOS apparatus of Sympatec AG/Germany, of exposing a powder sample, which has been injected by compressed air, to a laser light and determining the volume average particle size from its diffraction strength. According to, for example, page 88 of "Kaitei Zoho Funtai Bussei Zusetsu (revised and enlarged edition of Illustration of Powder Properties" edited by Funtai Kogakukai and Nippon Funtai Kogyogijutsu Kyokai, published by Nikkei Gijutsu Tosho Co., Ltd., 1985, the volume-average particle size is calculated by $\{\Sigma(nD^3)/\Sigma n\}^{1/3}$ wherein D is a particle diameter, n is the number of particles having the particle diameter, and $\Sigma n$ is a total number of particles.

The low-substituted hydroxypropyl cellulose to be used in the present invention is a kind of cellulose ether. Although it is analogous to the hydroxypropyl cellulose popularly employed as a binder, their properties are not the same. They differ essentially in the content of a hydroxypropoxyl group. The content of the former one is 5 to 16.0 wt %, while that of the latter one is 53.4 to 77.5 wt %. The content of the hydroxypropoxyl group is measured by the method as specified in Japanese Pharmacopoeia and its range is clearly specified by the monograph of "low-substituted hydroxypropyl cellulose" of Japanese Pharmacopoeia.

The low-substituted hydroxypropyl cellulose contains a hydroxypropoxyl group in an amount of 5.0 to 16.0 wt %.

The low-substituted hydroxypropyl cellulose having a loose bulk density of 0.40 g/ml or greater and a tapped bulk density of 0.60 g/ml or greater may be prepared as described below. First, pulp is immersed in an alkali solution to yield an alkali cellulose and then, this alkali cellulose is reacted with propylene oxide. The reaction product is charged in water or water adjusted to have alkalinity to completely dissolve the former in the latter. The substantially uniform, clear slurry thus obtained is then neutralized with hydrochloric acid. After collection of the low-substituted hydroxypropyl cellulose thus precipitated, it is washed with water, dried and then pulverized.

The term "completely dissolve" as used herein means that the product almost completely loses its shape in the solution. Therefore, it embraces not only a completely clear solution but also an unclear slurry or a slurry in which remaining of about 5 to 10 blobs per 3 liters can be recognized. After dissolution, the product is in the form of a highly viscous slurry which requires a kneading device having a high stirring power such as kneader. By neutralization with an acid such as hydrochloric acid, low-substituted hydroxypropyl cellulose is precipitated, followed by collection, washing, drying and pulverization, whereby the low-substituted hydroxypropyl cellulose of the present invention can be obtained.

In the preferred embodiment of the present invention, employed is a low-substituted hydroxypropyl cellulose having a volume average particle size, as measured by the dry laser diffraction method, of 25 $\mu$m or less which is obtained by pulverizing a low-substituted hydroxypropyl cellulose having a loose bulk density of 0.40 g/ml or greater (more preferably, 0.40 g/ml or greater but less than 0.60 g/ml), a tapped bulk density of 0.60 g/ml or greater (more preferably, 0.60 g/ml or greater but less than 0.85 g/ml) and a volume average particle size, as measured by the above-described diffraction method, of 30 $\mu$m or greater (more preferably, 30 to 200 $\mu$m). The low-substituted hydroxypropyl cellulose thus obtained is preferred to have a loose bulk density of 0.29 g/ml or greater (more preferably, 0.29 g/ml or greater but less than 0.55 g/ml) and a tapped bulk density of 0.55 g/ml or greater (more preferably, 0.55 g/ml or greater but less than 0.85 g/ml).

In the present invention, the low-substituted hydroxypropyl cellulose is added in an amount of 1 to 99 parts by weight, preferably 5 to 50 parts by weight, in 100 parts by weight of the solid preparation. Amounts of the low-substituted hydroxypropyl cellulose less than 1 part by weight may make it difficult to handle the tablet because of insufficient strength, while those exceeding 99 parts by weight may cause a delay in disintegration of the tablet in the oral cavity in spite of imparting the tablet with sufficient strength.

In the present invention, the term "sugar and/or sugar alcohol" as used herein means a sugar in a wide sense which includes a sugar alcohol. Sugar is a generic name of carbohydrates which are soluble in water and have a sweet taste, and includes monosaccharides and a large number of oligosaccharides. Polysaccharides are also included in the term "sugar" because they are hydrolyzed into a sugar. The term "sugar alcohol" means a polyhydric alcohol formed by reduction of the carbonyl group of a sugar and it also includes cyclic sugar alcohols (cyclitols) having analogous properties.

In the present invention, preferred examples of the sugar or sugar alcohol include erythritol, sorbitol, trehalose, xylitol, mannitol, glucose and sucrose, with erythritol, sorbitol, trehalose and xylitol being particularly preferred. They may be used either singly or in combination.

These sugars or sugar alcohols are used in the crystalline or powdery form. Use of those having an average particle size of 500 $\mu$m or less impairs the resulting solid preparation with excellent properties in formability or moldability, disintegration and texture.

The sugar and/or sugar alcohol is added in an amount of 1 to 99 parts by weight, preferably 10 to 90 parts by weight in 100 parts by weight of the solid preparation. At an amount of the sugar and/or sugar alcohol less than 1 part by weight, it may take a longer time for the resulting tablet to be disintegrated in the oral cavity, while at an amount exceeding 99 parts by weight, the strength of the resulting preparation may become insufficient.

There is no particular limitation imposed on the kind of the main component to be incorporated in the solid preparation of the present invention insofar as it is a pharmaceutical. For example, an analgesic-antipyretic, antibiotic, anti-inflammatory, vitamin or nutrient may be incorporated.

Another ingredient such as lubricant, binder, stabilizer, colorant or corrigent may also be added.

The solid preparation of the present invention may be produced by mixing the above-described ingredients and then treating the resulting mixture by direct tableting or dry tableting. Or a method such as dry granulation, fluidized bed granulation or wet granulation may be employed.

The tableting for the formation of tablets may be conducted using an apparatus ordinarily employed for the formation or granulation of tablets. Examples may include single-punch tableting machine, rotary tableting machine and tableting tester.

Upon tableting, formation is conducted usually under a pressure of 50 to 300 MPa, preferably 80 to 200 MPa. At an pressure less than 50 MPa, the resulting tablet may have insufficient hardness, which disturbs easy handling, while pressures exceeding 300 MPa may happen to cause a delay in disintegration.

The solid preparation, particularly, orally disintegrating tablet thus produced is excellent in disintegration in the oral cavity and retains proper formability or moldability (strength). More specifically, the disintegration time in the oral cavity (time until the tablet completely dissolves with the saliva of a normal adult in the oral cavity) of the solid preparation of the present invention is usually 1 to 60 seconds, preferably 1 to 40 seconds, more preferably 1 to 30 seconds. The hardness of the tablet (as measured by tablet hardness tester) is usually about 2 to 15 kgf, preferably 3 to 10 kgf.

The solid preparation of the present invention embraces tablets, granules, fine subtilaes and capsules.

Examples and Comparative Examples of the present invention will be described below. However, these examples are not to be construed to limit the scope of the invention.

EXAMPLE 1

After 70 parts by weight of powder obtained by pulverizing Erythritol (product of Nikken Chemicals Co., Ltd.) in a mortar and shifting it through a sieve having an opening of 355 μm and 30 parts by weight of a low-substituted hydroxypropyl cellulose (having a volume average particle size, as measured by the dry laser method, of 47 μm, a loose bulk density of 0.47 g/ml, a tapped bulk density of 0.69 g/ml and a hydroxypropoxyl content of 11.0 wt %) were mixed, magnesium stearate was added thereto in 0.5 wt % based on the weight of the resulting mixture. Then, the mixture was compressed at 100 MPa by using a single-punch tableting machine ("Tableting tester", manufactured by Sankyo Biotech Co., Ltd.), whereby a solid preparation of 11 mm Ø and 480 mg/tablet was obtained.

EXAMPLE 2

After 70 parts by weight of powder obtained by pulverizing Erythritol in a mortar and shifting it through a sieve having an opening of 355 μm and 30 parts by weight of a low-substituted hydroxypropyl cellulose (obtained by finely pulverizing the low-substituted hydroxypropyl cellulose obtained in Example 1 and having a volume average particle size, as measured by the dry laser method, of 16 μm) were mixed, magnesium stearate added thereto in 0.5 wt % based on the weight of the resulting mixture. Then, the mixture was compressed at 100 MPa by using a single-punch tableting machine, whereby a solid preparation of 11 mm Ø and 480 mg/tablet was obtained.

EXAMPLE 3

After 70 parts by weight of powder obtained by pulverizing Erythritol in a mortar and shifting it through a sieve having an opening of 355 μm and 30 parts by weight of the low-substituted hydroxypropyl cellulose of Example 1 were mixed, purified water was sprayed to the resulting mixture by using a fluidized-bed granulator ("Multiplex MP-01", manufactured by Pawrex Corporation), whereby fluidized-bed granulation was conducted. Magnesium stearate was then added in 0.5 wt % based on the resulting granulated powders. Then, the mixture was compressed at 100 MPa by using a single-punch tableting machine, whereby a solid preparation of 11 mm Ø and 480 mg/tablet was obtained.

EXAMPLE 4

After 70 parts by weight of powder obtained by pulverizing erythritol in a mortar and shifting it through a sieve having an opening of 355 μm and 30 parts by weight of the low-substituted hydroxypropyl cellulose of Example 2 were mixed, purified water was sprayed to the resulting mixture by using a fluidized-bed granulator ("Multiplex MP-01" manufactured by Pawrex Corporation), whereby fluidized-bed granulation was conducted. Magnesium stearate was then added in 0.5 wt % based on the resulting granulated powders. Then, the mixture was compressed at 100 MPa by using a single-punch tableting machine, whereby a solid preparation of 11 mm Ø and 480 mg/tablet was obtained.

EXAMPLE 5

In a similar manner to Example 4 except for a change of the compression force to 200 MPa, an orally disintegrating tablet was obtained.

COMPARATIVE EXAMPLE 1

To the powder obtained by pulverizing erythritol in a mortar and shifting it through a sieve having an opening of 355 μm was added 0.5 wt % of magnesium stearate based on the powder, followed by compression at 100 MPa by using a single-punch tableting machine, whereby a solid preparation of 11 mm Ø and 480 mg/tablet was obtained.

COMPARATIVE EXAMPLE 2

After 70 parts by weight of powder obtained by pulverizing erythritol in a mortar and shifting it through a sieve having an opening of 355 μm and 30 parts by weight of a low-substituted hydroxypropyl cellulose ("LH-21" manufactured by Shin-Etsu Chemicals Co., Ltd., having a volume average particle size, as measured by the dry laser method, of 37 μm, a loose bulk density of 0.335 g/ml, a tapped bulk density of 0.597 g/ml and a hydroxypropoxyl content of 10.9 wt %) were mixed, magnesium stearate was added in 0.5 wt % based on the resulting mixture. Then, the mixture was compressed at 100 MPa by using a single-punch tableting machine, whereby orally disintegrating tablets, each 11 mm Ø and 480 mg per tablet, were obtained.

COMPARATIVE EXAMPLE 3

After 70 parts by weight of powder obtained by pulverizing erythritol in a mortar and shifting it through a sieve having an opening of 355 μm and 30 parts by weight of the low-substituted hydroxypropyl cellulose of Comparative Example 2 were mixed, purified water was sprayed to the resulting mixture, whereby fluidized-bed granulation was conducted. Magnesium stearate was then added in 0.5 wt % based on the resulting granulated powders. Then, the resulting mixture was compressed at 100 MPa by using a single-punch tableting machine, whereby orally disintegrating tablets, each 11 mm Ø and 480 mg per tablet, were obtained.

COMPARATIVE EXAMPLE 4

In a similar manner to Comparative Example 3 except for the use of a low-substituted hydroxypropyl cellulose ("LH-31" manufactured by Shin-Etsu Chemicals Co., Ltd., having a volume average particle size, as measured by the dry laser method, of 17 μm, a loose bulk density of 0.323 g/ml, a tapped bulk density of 0.623 g/ml and a hydroxypropoxyl content of 10.9 wt. %), an orally disintegrating tablet was obtained.

COMPARATIVE EXAMPLE 5

In a similar manner to Comparative Example 3 except for the use of a low-substituted hydroxypropyl cellulose ("LH-32" manufactured by Shin-Etsu Chemicals Co., Ltd., having a volume average particle size, as measured by the dry laser method, of 18 μm, a loose bulk density of 0.306 g/ml, a tapped bulk density of 0.582 g/ml and a hydroxypropoxyl content of 8.3 wt %), an orally disintegrating tablet was obtained.

The hardness and disintegration time of the obtained tablets in each of Examples 1 to 5 and Comparative Examples 1 to 5 were measured. The results are shown in Table 1. The hardness of the orally disintegrating tablets was measured using a tablet hardness tester (Elveca hardness tester), while the disintegration time was measured using a disintegration tester specified in Japanese Pharmacopoeia (test liquid: water, 37° C.) at n=6 (n standing for the number of samples). The disintegration time in the oral cavity was evaluated by 5 normal male and female adults. It was determined by the time until the tablet dissolves or disintegrates completely in their oral cavity when they keep it lightly within their mouth without chewing it. The average value was calculated. At the same time, feeling upon use was also evaluated. Evaluation was made based on four grades, that is, excellent (A), good (B), fair (C) and poor (D).

From the results of Table 1, it has been found that in the relationship between the hardness and disintegration time, each of the solid preparations of the present invention shows rapid disintegration and good texture in the oral cavity.

TABLE 1

| | Hardness (kgf) | Disintegration test (J.P.) (second) | Disintegration time in the oral cavity (second) | Feeling upon use * |
|---|---|---|---|---|
| Example 1 | 2 | 8 | 37 | B |
| Example 2 | 4 | 18 | 41 | B |
| Example 3 | 2 | 6 | 21 | B |
| Example 4 | 4 | 8 | 21 | A |
| Example 5 | 6 | 11 | 27 | A |
| Comparative Example 1 | unmeasurable | — | — | — |
| Comparative Example 2 | 2 | 8 | 45 | D |
| Comparative Example 3 | 3 | 12 | 47 | C |
| Comparative Example 4 | 4 | 14 | 50 | C |
| Comparative Example 5 | 6 | 20 | 130 | D |

* A: excellent, B: good, C: fair, D: poor

What is claimed is:

1. A process for producing a solid preparation, comprising:

pulverizing a low-substituted hydroxypropyl cellulose containing a hydroxypropoxyl group in an amount of 5.0 to 16.0 wt % having a loose bulk density of 0.40 g/ml or greater as determined by uniformly feeding a sample downwards from a height of 23 cm to a cylindrical container of 5.03 cm in diameter and 5.03 cm in height through a 24 mesh JIS sieve, leveling the upper surface and weighing the sample, a tapped bulk density of 0.60 g/ml or greater as determined by placing a cap on the container, adding additional sample up to an upper edge of the cap and tapping from a height of 1.8 cm 180 times, removing the cap and leveling and weighing the sample, and a volume avenge particle size as measured by dry laser diffraction of 30 μm or less to form low-substituted hydroxypropyl cellulose having an average particle size of 25 μm or less; and mixing the low-substituted hydroxypropyl cellulose with an average particle sin of 25 μm or loss with a sugar or sugar alcohol or both.

2. A solid preparation prepared by Conning a mixture comprising a low-substituted hydroxypropyl cellulose containing a hydroxypropoxyl group in an amount of 5.0 to 16.0 wt % having a loose bulk density of 0.40 g/ml or greater as determined by uniformly feeding a sample downwards from a height of 23 cm to a cylindrical container of 5.03 cm in diameter and 5.03 cm in height through a 24 mesh JIS sieve, leveling the upper surface and weighing the sample, and a tapped bulk density of 0.60 g/ml or greater as determined by placing a cap on the container, adding additional sample up to an upper edge of the cap and tapping from a height of 1.8 cm 180 times, removing the cap and leveling and weighing the sample, and at toast one sugar or sugar alcohol, or both, wherein said sugar or sugar alcohol or both has an average particle size of 500 μm or less and is selected from the group consisting of erythritol, sorbitol, xylitol, mannitol, glucose, sucrose and mixtures thereof.

3. A solid preparation prepared by forming a mixture comprising a low-substituted hydroxypropyl cellulose containing a hydroxypropoxyl group in an amount of 5.0 to 16.0 wt % having a volume average particle size as measured by dry laser diffraction of 25 μm or less, which is obtained by pulverizing a low-substituted hydroxypropyl cellulose having a loose bulk density of 0.40 g/ml or greater as determined by uniformly feeding a sample downwards from a height of 23 cm to a cylindrical container of 5.03 cm in diameter and 5.03 cm in height through a 24 mesh JIS sieve, leveling the upper surface and weighing the sample, a tapped bulk density of 0.60 g/ml or greater as determined by placing a cap on the container, adding additional sample up to an upper edge ortho cap and tapping from a height of 1.8 cm 180 times, removing the cap and leveling and weighing the sample, and a volume average particle size as measured by dry laser diffraction of 30 μm or greater; and at least one sugar or sugar alcohol, or both, wherein said sugar or sugar alcohol or both has an average particle size of 500 μm or loss.

4. A solid preparation according to claim 3, wherein said sugar or sugar alcohol or both comprises at least one sugar or sugar alcohol or both selected from the group consisting of erythritol, sorbitol, trehalose, xylitol, mannitol, glucose, sucrose and mixtures thereof.

* * * * *

UNITED STATES PATENT AND TRADEMARK OFFICE
CERTIFICATE OF CORRECTION

PATENT NO. : 6,559,134 B2
DATED : May 6, 2003
INVENTOR(S) : Tanno et al.

It is certified that error appears in the above-identified patent and that said Letters Patent is hereby corrected as shown below:

Column 8,
Line 12, "avenge" should read -- average --;
Line 17, "sin" should read -- size --; "loss" should read -- less --;
Line 20, "Conning" should read -- forming --;
Line 32, "toast" should read -- least --;
Line 51, "ortho" should read -- of the --;
Line 57, "loss" should read -- less --.

Signed and Sealed this

Twenty-second Day of July, 2003

JAMES E. ROGAN
*Director of the United States Patent and Trademark Office*